United States Patent [19]

Levy

[11] Patent Number: 5,648,217
[45] Date of Patent: Jul. 15, 1997

[54] DNA SEQUENCE WHICH BINDS TRANSCRIPTIONAL REGULATORY PROTEINS ACTIVATED IN RESPONSE TO VARIOUS CYTOKINES AND USES THEREOF

[75] Inventor: David E. Levy, New York, N.Y.

[73] Assignee: New York University, New York, N.Y.

[21] Appl. No.: 458,364

[22] Filed: Jun. 2, 1995

Related U.S. Application Data

[62] Division of Ser. No. 394,191, Feb. 24, 1995, which is a continuation of Ser. No. 121,931, Sep. 15, 1993, abandoned.

[51] Int. Cl.[6] .............................. C12Q 1/68; G01N 33/53
[52] U.S. Cl. .............................. 435/6; 435/7.1; 435/69.8; 436/94; 436/501
[58] Field of Search .............................. 435/6, 7.1, 69.8; 436/501, 94

[56] References Cited

U.S. PATENT DOCUMENTS 5,273,883  12/1993  Saiki et al. .................................. 435/6
5,416,195  5/1995  Camble et al. .......................... 530/351

FOREIGN PATENT DOCUMENTS 9414980  7/1994  WIPO .

OTHER PUBLICATIONS

T.E. Hayes et al., "Inducible Binding of a Factor to the c–fos Regulatory Region", *Proc. Natl. Acad. Sci. USA* 84:1272–1276 (1987).

B.J. Wagner et al., "The SIF Binding Element Confers sis/PDGF Inducibility Onto the c-fos Promoter", *EMBO J.* 9:4477–4484 (1990).

R.N. Pearse et al., "Interferon γ–Induced Transcription of the High–Affinity Fc Receptor for IgG Requires Assembly of a Complex that Includes the 91–kDa Subunit of Transcription Factor ISGF3", *Proc. Natl. Acad. Sci. USA* 90:4314–4318 (1993).

S.A. Veals et al., "Subunit of an Alpha–Interferon–Responsive Transcription Factor Is Related to Interferon Regulatory Factor and Myb Families of DNA–Binding Proteins", *Mol. Cell. Biol.* 12:3315–3324 (1992).

S.A. Veals, S.A. et al., "Two Domains of ISGF3γ That Mediate Protein–DNA and Protein–Protein Interactions during Transcription Factor Assembly Contribute to DNA–Binding Specificity", *Molec. Cell. Biol.* 13:196–206 (1993).

D.E. Levy et al., "Interferon–Dependent Transcriptional Activation: Signal Transduction Without Second Messenger Involvement", *New Biologist* 2:923–928 (–1990).

D.S. Kessler et al., "Interferon–α Regulates Nuclear Translocation and DNA–Binding Affinity of ISGF3, a Multimeric Transcriptional Activator", *Genes Dev.* 4:1753–1765 (1990).

Y. Kanno et al., "The Genomic Structure of the Murine ICSBP Gene Reveals the Presence of the Gamma Interferon–Responsive Element, to Which an ISGF3α Subunit (or Similar) Molecule Binds", *Molec. Cell. Biol.* 13:3951–3963 (1993).

Y. Kanno et al., "Binding of p91/ISGF3α to a Palindromic cis–Element Mediates IFN–γ Induced Transcription of Genes in the IRF Family", *J. Cell. Biochem.* Supp. 18B:238 (abstr. 1230) (1994).

(List continued on next page.)

*Primary Examiner*—Kenneth R. Horlick
*Attorney, Agent, or Firm*—Morrison & Foerster LLP

[57] ABSTRACT

An oligonucleotide comprising the DNA sequence TTTC-CNGGAAA (SEQ ID NO:1) in single stranded or double stranded form, or a derivative thereof, binds to transcriptional regulatory proteins induced by cytokines, growth factors or hormones. Such oligonucleotides are useful in detecting, identifying or purifying transcriptional regulatory proteins. Recombinant DNA constructs comprising the oligonucleotide sequence operably linked to a promoter and a reporter DNA sequence and cells transfected therewith are also disclosed. Also disclosed are DNA-binding proteins other than p 91 which are inducible in a cell by a cytokine, growth factor or hormone, and which, when tyrosine phosphorylated, bind to the above oligonucleotide DNA sequence.

3 Claims, 5 Drawing Sheets

OTHER PUBLICATIONS

S.H. Sims et al., "A Novel Interferon–Inducible Domain: Structural and Functional Analysis of the Human Interferon Regulatory Factor 1 Gene Promoter", *Molec. Cell. Biol.* 13:690–702 (1993).

C. Schindler et al., "Interferon–Dependent Tyrosine Phosphorylation of a Latent Cytoplasmic Transcription Factor", *Science* 257:809–913 (1992).

K. Shuai et al., "Activation of Transcription of IFN-γ: Tyrosine Phosphorylation of a 91–kD DNA Binding Protein", *Science* 258:1808–1812 (1992).

M. J. Gutch et al., "Tyrosine Phosphorylation is Required for Activation of an αInterferon–Stimulated Transcription Factor", *Proc. Natl. Acad. Sci. USA* 89:11411–11415 (1992).

D.J. Lew et al., "Overlapping Elements in the Guanylate–Binding Protein Gene Promoter Mediate Transcriptional Induction by Alpha and Gamma Interferons", *Molec. Cell. Biol.* 11:182–191 (1991).

U.M. Wegenka et al., "Acute–Phase Response Factor, a Nuclear Factor Binding to Acute–Phase Response Elements, Is Rapidly Activated by Interleukin–6 at the Posttranslational Level", *Molec. Cell. Biol.* 13:276–288 (1993).

K–I. Igarashi et al., "In Vitro Activation of a Transcription Factor by Gamma Interferon Requires a Membrane–Associated Tyrosine Kinase and Is Mimicked by Vanadate", *Molec. Cell. Biol.* 13:3984–3989 (1993).

Larner et al., "Tyrosine Phosphorylation of DNA Binding Protein by Multiple Cytokines," *Science* 261:1730–33 (1993).

Fu et al., "ISGF3, The Transcriptional Activator Induced by Interferon α, Consists of Multiple INteracting Polypeptide Chains," Proc Natl Acad Sci USA 87:8555–59 (1990).

Wegenka et al., *Mol. Cell. Biol.* 13(1), 276–288 (1993).

Kanno et al., *Mol. Cell. Biol.* 13(7), 3951–3963 (1993).

DSE competes more efficiently

DNA SEQUENCE WHICH BINDS TRANSCRIPTIONAL REGULATORY PROTEINS ACTIVATED IN RESPONSE TO VARIOUS CYTOKINES AND USES THEREOF

This application is a division of application Ser. No. 08/394,191 filed Feb. 24, 1995 which is a continuation of application Ser. No. 08/121,931 filed Sep. 15, 1993, abandoned.

This invention was funded in part by research grant AI 28900 from the National Institutes of Health, which provides to the United States Government certain rights in this invention.

BACKGROUND OF THE INVENTION

1. Field of the Invention

The present invention relates to DNA oligonucleotides that bind specifically to transcriptional regulatory proteins (TRPs) and the use of such oligonucleotide sequences in (a) the detection and/or isolation of TRPs, (b) analysis of TRP induction by cytokines and (c) analysis of TRP action.

2. Description of the Background Art

Cell surface receptors for extracellular polypeptide ligands are widely expressed on most mammalian cells and serve to transduce proliferative and differentiation signals to the cell's interior. Multistep signaling pathways lead from the binding of growth factor receptors, for example, the epidermal growth factor receptor (EGFR) to subsequent intracellular processes (J. Schlessinger et al., *Neuron* 9, 383 after ligand activation, autophosphorylate the receptor cytoplasmic tail and phosphorylate other cellular substrates (A. Ullrich et al., *Cell* 61, 203 (1990)).

A common response for receptor and non-receptor signaling pathways involves the activation of Ras (L. S. Mulcahy et al., *Nature* 313, 241 (1985)). Autophosphorylated EGFR serves as a docking site for SH2 domain-containing proteins (C. A. Koch et al., *Science* 252, 668 (1991), which lead to Ras activation (E. J. Lowenstein et al., *Cell* 70, 431 (1992); N. Li et al., *Nature* 363, 85 (1993); N. W. Gale et al., *Nature* 363, 88 (1993); M. Rozakis-Adcock et al., *Nature* 363, 83 (1993); S. E. Egan et al., *Nature* 363, 45 (1993); M. Rozakis-Adcock et al., *Nature* 360, 689 (1992); K. Baltensperger et al., *Science* 260, 1950 (1993); J. P. Olivier et al., *Cell* 73, 179 (1993)). Activated Ras then initiates a cascade of serine/threonine phosphorylations through Raf and MAP kinases (S. A. Moodie et al., *Science* 260, 1658 (1993); C. A. Lange-Carter et al., *Science* 260, 315 (1993)) leading to phosphorylation of nuclear proteins (C. S. Hill et al., *Cell* 73, 395 (1993); H. Gille et al., *Nature* 358, 414 (1992); R. H. Chen et al., *Mol. Cell. Biol.* 12, 915 (1992)).

It is widely speculated that the biological consequences of receptor tyrosine kinase activation depends on changes in gene expression. However, it has been difficult to document a direct connection between the cytoplasmic phosphorylation events stimulated by receptor tyrosine kinase activation and modulation of nuclear transcription factors. In contrast, recent studies of signals generated by interferons (IFNs) have revealed an apparently simpler path to the nucleus (D. E. Levy et al., *New Biologist* 2, 923 (1990)). Though lacking intrinsic catalytic domains (G. Uzé et al., *Cell* 60, 225 (1990)), IFNα receptors stimulate tyrosine phosphorylation of a family of proteins that serve as DNA-binding and transcriptional-activating factors (C. Schindler et al., *Science* 257, 809 (1992); K. Shuai et al., *Science* 258, 1808 (1992); M. J. Gutch et al., *Proc. Natl. Acad. Sci. USA* 89, 11411 (1992)). These proteins, generically termed "signal transducers and activators of transcription (STATs)," normally sequestered in the cytoplasm (D. E. Levy et al., *Genes Dev.* 3, 1362 (1989); D. S. Kessler et al., *Genes Dev.* 4, 1753 (1990)), upon tyrosine phosphorylation, assemble into a multimeric complex, translocate to the nucleus, and bind cis-acting enhancer elements in the appropriate regulatory regions. One example of a STAT is ISGF3 which binds to regulatory regions of IFN-stimulated genes. IFNγ stimulates phosphorylation of the 91 kDa protein subunit of ISGF3 (termed p91), leading to its appearance in the nucleus and its binding to a distinct genetic element, activating IFNγ-responsive genes (K. Shuai et al., supra).

When mouse 3T3 fibroblasts are stimulated by v-sis (platelet-derived growth factor or PDGF), a nuclear factor, termed sis-inducible factor (SIF), binds to a DNA sequence which is a regulatory element in the c-fos promoter (T. E. Hayes et al., *Proc. Natl. Acad. Sci. USA* 84, 1272 (1987); B. J. Wagner et al., *EMBO J.* 9, 4477 (1990)). The rapid, transient stimulation of this DNA-binding activity led the present inventor and his colleagues to investigate its possible relationship to ISGF3 activation. This, led the present inventor to the discovery of the subject matter of the present invention, including (1) novel DNA oligonucleotide sequences to which such TRPs bind and (2) uses for these oligonucleotides.

SUMMARY OF THE INVENTION

The present invention is directed to an oligonucleotide having between about 11 and 150 nucleotides and comprising the nucleotide sequence TTTCCNGGAAA [SEQ ID NO:1], which oligonucleotide binds directly or indirectly to the transcriptional regulatory protein p91. The above sequence is preferably TTTCCGGGAAA [SEQ ID NO:2].

The above oligonucleotide may be double stranded. A preferred double stranded oligonucleotide has the sequence:

| | |
|---|---|
| 5'-gatcTAGGGATTTCCGGGAAATGAAGCT-3' | SEQ ID NO:3 |
| 3'ATCCCTAAAGGCCCTTTACTTCGActag-5' | SEQ ID NO:4 |

The present invention is further directed to a composition useful for measuring the ability of a compound to stimulate transcription of DNA, which composition comprises a recombinant DNA molecule comprising an oligonucleotide as described above, operably linked to a promoter and to an expressible reporter nucleotide sequence.

Also provided is a host cell transfected with a composition as described above.

The present invention is further directed to a method for detecting the presence of a transcriptional regulatory protein in a sample, which protein is capable of binding to an oligonucleotide as described above, which method comprises:

(a) contacting the sample with an oligonucleotide as described above under conditions wherein the protein binds to the oligonucleotide to form a complex;

(b) detecting the presence of the protein-oligonucleotide complex, wherein the presence of the complex indicates the presence of the protein in the sample.

Also provided is a method for determining whether a protein is a DNA-binding protein with transcriptional regulatory protein activity, comprising detecting the direct or indirect binding of a protein in a sample containing the protein with an oligonucleotide as described above.

The present invention is directed to a method for detecting the presence or measuring the activity of a compound, in a sample, which compound is capable of inducing a transcriptional regulatory protein in a cell, wherein the transcriptional regulatory protein binds to DNA and stimulates transcription, which method comprises:

(a) contacting the sample with a host cell as described above under conditions in which the expressible DNA is expressed;

(b) measuring the expression of the DNA;

(c) comparing the expression in step (b) with the expression of expressible DNA not linked to the above oligonucleotide, wherein an increase in the expression of the expressible DNA indicates the presence in the sample of, or the activity of, the compound.

The present invention also provides a DNA-binding protein, other than p91, which protein, after tyrosine phosphorylation, binds to the DNA sequence TTTCCNG-GAAA (SEQ ID NO:1) or to a derivative thereof. The DNA binding protein may be inducible in a cell by a cytokine, growth factor or hormone. The DNA binding protein may be tyrosine phosphorylated in response to activation of a cell with a cytokine, growth factor or hormone. The cytokine, growth factor or hormone is preferably interleukin-2, interleukin-3 or erythropoietin.

In another embodiment, the above DNA-binding protein binds directly or indirectly to the double stranded DNA sequence 5'-gatcTAGGGATTTCCGGGAAATGAAGCT-3'  SEQ ID NO:3

3'ATCCCTAAAGGCCCTTTACTTCGActag-5'.  SEQ ID NO:4

The above DNA-binding protein is preferably a transcriptional regulatory protein.

Also provided is a method for isolating or purifying a DNA binding protein in a sample, which protein binds directly or indirectly to an oligonucleotide as described above, which method comprises:

(a) contacting the sample with an oligonucleotide as above under conditions wherein said protein binds to the oligonucleotide to form a complex, preferably, wherein the oligonucleotide is immobilized on a solid phase carrier;

(b) eluting the protein from the protein-oligonucleotide complex, thereby isolating or purifying the protein.

BRIEF DESCRIPTION OF THE DRAWINGS

FIGS. 1A–1E show stimulation of DNA-binding activity in response to growth factors. Cells were untreated or treated with the indicated growth factors and cytokines prior to detergent lysis and analysis of extracts by gel band shift using a labeled oligonucleotide containing an SIF-recognition sequence.

FIG. (1A) Swiss 3T3 mouse fibroblasts were treated for 15 min with 40 ng/ml human recombinant PDGF-BB for 15 min and fractionated into cytoplasmic and nuclear extracts. 5 μg of cytoplasmic and 10 μg of nuclear extracts were added to DNA binding reactions.

FIG. (1B) Human FS2 fibroblasts were treated with human recombinant EGF (250 ng/ml), PDGF (40 ng/ml), IFNα (500 U/ml), or IFNγ (1 ng/ml) for 15 min, as indicated.

FIG. 1(C) Human FS2 fibroblasts were treated for the indicated times with PDGF, IFNα, and IFNγ. Cells treated with cycloheximide (lanes 8, 16, and 24) were pretreated for 15 min and throughout stimulation with 50 μg/ml.

FIG. (1D) P13 cells overexpressing the human CSF1 receptor (lanes 1–5), WT7 cells overexpressing the flg FGF receptor (lanes 6–10), and 3006 cells expressing the human insulin receptor (lanes 11–13) were treated for 15 min, as indicated, with the following ligands: murine IFNα, 5000 u/ml; murine IFNγ, 5 ng/ml; human PDGF-BB, 50 ng/ml; human CSF1, 10000 u/ml; acidic FGF, basic FGF, and k-FGF, 200 ng/ml; bovine insulin, 1 μg/ml.

FIG. (1E) Extracts from human FS2 fibroblasts treated for 15 min with PDGF were analyzed by band shift using a modified SIF binding sequence recognizing SIF with higher affinity. Competitions were carried out using 100-fold molar excess of unlabeled oligonucleotide, as indicated. Antibodies against human p113, p91 carboxyl-terminal peptide or p48 were added at a final concentration of 1:200 for lanes 5–7, respectively.

FIG. (2A) Immunoprecipitation of $^{32}$P-orthophosphate-labeled (2 hr) extracts of human FS2 fibroblasts stimulated with the indicated factors for 10 min. Immunoprecipitates with anti-p91 antibody were analyzed by SDS-PAGE.

FIG. (2B) Phosphoamino acid analysis of labeled p91 excised from SDS-PAGE, hydrolyzed, and analyzed by thin-layer chromatography. Migration of phosphoamino acid standards is indicated at right.

FIG. (2C) Triptic phosphopeptide mapping of p91. Immunoprecipitated p91 from orthophosphate-labeled cells untreated or treated with IFNs or PDGF as indicated were digested with trypsin and analyzed by two-dimensional thin-layer electrophoresis and chromatography. Upon longer exposure, a fourth phosphopeptide fragment was detected in both unstimulated and stimulated samples.

FIG. (2D) FGF fails to induce tyrosine phosphorylation of p91. Immunoprecipitated p91 was analyzed by SDS-PAGE and immunoblotting using anti-phosphotyrosine (lanes 1–3) or anti-p91 (lanes 4–6) antibodies (26).

FIG. (3A) Transfected mouse cells stably expressing wild-type human EGF receptor (HER14, lanes 1–3), no human receptor (3T3, lanes 4 and 5), mutant receptors having the five major phosphotyrosine sites converted to phenylalanine (Y5F, lanes 6 and 7), or mutant receptor truncated in the cytoplasmic tail at amino acid 991 (D991, lanes 8 and 9) were treated with mouse IFNα (2500 U/ml) or human EGF (250 ng/ml) for 15 min, as indicated, and nuclear extracts were analyzed by band shift.

FIG. (3B) Detergent lysates of the same cell lines were analyzed by immunoblotting for the presence of the human EGF receptor using rabbit anti-EGFR antiserum FIG. (3C) Rat L6 myoblasts (lanes 1 and 2) or L6 cells stably transfected with dominant-negative Asn-17 Ras under a hormone-responsive promoter and induced with 1.5 μM dexamethasone overnight (lanes 3 and 4) were treated with PDGF, as indicated. Extracts were analyzed for p91 activation by band shift (top) or for Ras expression by immunoblotting (bottom).

FIG. (3D) Extracts from (C) were analyzed for MAP kinase activation by immunoblotting with anti-phosphotyrosine serum.

FIG. 4 presents a model for rapid signal transduction in response to EGF. Autophosphorylation of the cytoplasmic tail of EGFR following EGF stimulation could create a docking site either for p91 directly or for a cytoplasmic kinase, such as a member of the Jak/Tyk family, leading to tyrosine phosphorylation of p91. Activated p91 directly translocates to the nucleus and binds DNA, in contrast to the Ras-dependent pathway where multiple steps are required to induce Ser/Thr phosphorylation of diverse nuclear proteins.

FIG. 5 shows that proteins bind the DSE sequence with higher affinity than to the SIE. Nuclear extracts (5 µg) from Swiss 3T3 cells treated for 15 min with 2500 u/ml murine IFNα, were mixed with labeled DSE in a 5 µl gel band shift reaction. Each reaction contained 1.8 µg of non-specific competitor DNA plus the indicated molar excess of competitor oligonucleotide. Gel band shift reactions were resolved on 5% acrylamide gels. Tenfold molar excess of DSE competed equally to 50-fold excess of SIE. ns, the SRF binding site from the human gamma actin promoter; SIE, mutant sequence from the c-fos promoter defined by Wagner et al. (1990) EMBO J. 9:4477–4484 (1990); DSE, the DSE standard oligonucleotide.

FIG. 6 shows that DSE-binding proteins are induced by erythropoietin, IL2 and IL3. Nuclear extracts (5 µg) from BaF3/ER cells (D'Andrea et al. (1991) Molec. Cell. Biol. 11:1980–1987) or from LyD9 cells grown for 4 hr in the absence of IL3 or from CTLL cells (ATCC TIB214) grown for 4 hr in the absence of IL2, treated as indicated, were analyzed by band shift using a DSE probe.

DESCRIPTION OF THE PREFERRED EMBODIMENTS

The present inventor and his coworkers, studying the relationship between growth factor receptor tyrosine kinases and nuclear regulatory events, found that several polypeptide growth factors stimulate (1) tyrosine phosphorylation of p91, a transcriptional regulatory protein (TRP), (2) nuclear accumulation of p91 and (3) binding of p91 to DNA. The term "transcriptional regulatory protein" as used herein, is intended to include proteins that bind DNA either directly or indirectly through adaptor proteins, to modulate the transcriptional activity of the associated gene or genes. Understanding of, and manipulation of, these protein-DNA interactions require the ability to measure the binding of known and yet undiscovered TRPs to specific DNA sequences. Thus, the term "DNA-binding protein" as used herein refers either to a protein which binds directly to DNA (or to an oligonucleotide) or a protein which binds indirectly to DNA by binding to another protein which binds to or is bound to DNA (Veals, S. A. et al., Molec. Cell. Biol. 13:196–206 (1993)).

The term "activated" or "activation" as used herein, for example, "activation" of a cell by a cytokine, growth factor or hormone, means that one or more proteins in the cell are modified post-translationally such that they can now bind to DNA in a sequence-specific manner, preferably to the oligonucleotide sequence of the present invention. Such modification preferably comprises tyrosine phosphorylation of the protein. "Induction" of a protein, for example by a cytokine, growth factor or hormone, indicates that the abundance of the protein in the cell increases.

In performing the above studies, the present inventor, using synthetic oligonucleotides, discovered DNA sequences that serve as a binding site for cellular proteins that are induced or activated in response to a variety of biological stimuli. In particular these DNA sequences recognizes (or are recognized by) a family of transcriptional regulatory proteins (TRPs) that are activated in response to any of a variety of cytokines and growth factors. Such DNA sequences may be native sequences, or preferably, are non-native oligonucleotide sequences which bind more strongly to TRPs than do the native sequences.

A preferred DNA sequence according to the present invention is a dyadic symmetry element (DSE), having the sequence TTTCCNGGAAA (SEQ ID NO:1), or preferably, TTTCCGGGAAA (SEQ ID NO:2), that has higher binding affinity for TRPs than any other DNA sequence known. Therefore, this nucleotide sequence, preferably in the form of an oligonucleotide of between about 11 and 150 nucleotides, or a derivative thereof, is useful for detecting such TRPs in various biological samples, for purifying such TRPs, and for identifying new TRPs which bind to this sequence motif. While a GENBANK search revealed the presence of TTTCCGGGAAA (SEQ ID NO:2) in a number of published genome sequences, none of these sequences were as short as 11 to 150 nucleotides. Preferably, the oligonucleotides of the present invention are prepared synthetically using methods well-known in the art.

Furthermore, the novel oligonucleotides of the present invention are useful in the construction of expression vectors, such as plasmids, and host cells transfected therewith, which are useful for testing the biological activity of TRPs and for evaluating the ability of a compound, such as a potential drug, for its ability to stimulate or inhibit (a) induction of a TRP, (b) binding of a TRP to DNA or (c) transcriptional regulatory activity of the TRP.

Table I, below, lists a series of DNA sequences which have been shown by others, or discovered by the present inventors, to bind TRPs.

TABLE I

DNA SEQUENCES WHICH BIND TRANSCRIPTIONAL REGULATORY PROTEINS

| Name | SEQUENCE | SEQ ID NO: |
|------|----------|------------|
| FOS | GTTCCCGTCAA | 5 |
| SIE | TTTACGGGAA | 6 |
| GBP | TTTAGAGTAAT | 7 |
| MIG | TTTATAGTAAG | 6 |
| FCγ | TTTCTGGGAAA | 9 |
| K17 | ATTTGGAGAAA | 10 |
| IFN | GAAANN × 2* | |
| IFN | | |
| (ICSBP) | AGTGATTTCTCGGAAAGAGAG | 11 |
| (IRF-1) | CATCATTTCGGGGAAATCAGG | 12 |
| IFNγ | TT(C/A)CNNNAA | |
| IL-6 | TT(C/A)CNG(G/T)AA | |
| DSE | TTTCCGGGGAA | 2 |

*Two GAAANN motifs in inverted fashion, wherein N may be any nucleotide.

The present inventors discovered that the pattern of known or potential p91-binding DNA sequences predicted a trend towards a perfectly symmetric sequence such as the DSE, which is symmetric around an "odd" nucleotide (shown in brackets):

TTTCC[G]GGAAA     (SEQ ID NO:2)

AAAGG[G]CCCTT     (SEQ ID NO:13).

A preferred double stranded DNA sequence useful according to the present invention, which includes the DSE, has the sequence:

5'-gatcTAGGGA<u>TTTCCGGGAAA</u>TGAAGCT-3'   SEQ ID NO:3

3'ATCCCTA<u>AAAGGCCCTTT</u>ACTTCGActag-5'   SEQ ID NO:4

(The DSE sequence, or its complement, is underlined).

A preferred derivative of the oligonucleotide of the present invention is a multimer, comprising two or more "units" of the basic oligonucleotide. There is no limit to the number of such oligonucleotide units in a multimer although, for practical reasons, 2–10 units are preferred. The muitimeric embodiment is useful both as a probe for detecting a TRF, or for purifying a TRF. In addition, the recombinant DNA molecules disclosed herein (see below) comprising the oligonucleotide sequence of the present invention operably linked to a promoter and reporter sequence, may have two or more units or the oligonucleotide sequence present as an enhancer, either contiguously or with unrelated nucleotides intervening between units of the oligonucleotide.

A number of cytokines and/or growth factors activate proteins which bind the DSE or derivative DNA sequence of the present invention. These cytokines, growth factors and hormones include, but are not limited to, the interleukins IL2, IL3, IL4, IL5, IL6, and IL11, granulocyte-macrophage colony stimulating factor (GM-CSF), colony stimulating factor-1 (CSF-1), IFNα, IFNβ, IFNγ, epidermal growth factor (EGF), platelet derived growth factor (PDGF), leukemia inhibitory factor (LIF), oncostatin, nerve growth factor (NGF), ciliary neurotrophic factor (CNTF) and brain-derived neurotrophic factor (BDNF), erythropoietin, growth hormone, and prolactin. Thus, an oligonucleotide of the present invention is useful for detecting the presence of, or isolating, a TRP induced by any of these cytokines or growth factors.

As different cytokines may induce different TRPs with different DNA binding specificity, the oligonucleotide of the present invention is expected to detect new TRPs with binding specificity to DNA which are not identical to the TRPs characterized thus far. Furthermore, the oligonucleotide of the present invention is useful for the purification and characterization of such new TRPs.

A nuclear factor, termed sis-inducible factor (SIF), binds to a regulatory element in the c-fos promoter in response to v-sis (=PDGF) in mouse 3T3 fibroblasts (Hayes et al., supra; Wagner et al., supra This DNA binding activity is rapidly and transiently stimulated by PDGF. SIF binds a $^{32}$P-labeled, double-stranded oligonucleotide probe with the sequence 5'-GATCAGCTTCATTTCCCGTAAATCCCTA-3' (SEQ ID NO:14], which contains (in the complementary strand to the underlined region) the recognition sequence TTTACGGGAA (SEQ ID NO:6) designated SIE (sis-inducible element) in Table I, above.

To detect the binding of a protein to this SIE sequence, or to a novel DNA sequence of the present invention, the following approach may be used. Cells, such as 3T3 cells, are treated with an appropriate cytokine or growth factor, for example, with PDGF for 15 minutes to induce one or more TRPs. Extracts of the nucleus and cytoplasm are prepared using conventional methods and tested for binding to the oligonucleotide sequence by an electrophoretic band shift assay, such as that described by D. E. Levy et al., Genes Dev. 3, 1362 (1989) and D. S. Kessler et al., Genes Dev. 4, 1753 (1990)).

Little or no specific DNA binding activity is expected in extracts from untreated cells, whereas stimulated cells should possess significant activity. As described in the Examples, below, DNA binding activity may be found in both cytoplasmic and nuclear fractions. Furthermore, latent DNA binding activity may be stimulated in vitro by treating a cytoplasmic extract, supplemented with membranes, with the activating agent, for example a cytokine.

If an antibody specific for a TRP is available, it can be used to specifically interfere with DNA binding of the TRP, thereby assisting in the identification of the TRP. Furthermore, an unknown TRP identified or purified using the oligonucleotide of the present invention can be used to immunize animals to prepare an antibody specific for the TRP using methods well-known in the art. See, for example, Hartlow, E. et al., Antibodies: A Laboratory Manual., Cold Spring Harbor Laboratory Press, Cold Spring Harbor, N.Y., 1988)

The DNA sequence of the present invention thus can serve as a "probe sequence" similar to those used in a variety of nucleic acid detection systems well-known in the art. Here, however, such DNA probes are used to detect a protein, rather than a nucleic acid, which specifically binds to the DNA sequence.

The sensitivity of nucleic acid detection assays are increased by altering the manner in which detection is reported or signaled to the observer. Thus, for example, assay sensitivity can be increased through the use of detectably labeled oligonucleotide reagents. A wide variety of such labels have been used for this purpose including enzyme labels (Kourilsky et al. (U.S. Pat. No. 4,581,333), radioisotopic labels (Falkow et al. (U.S. Pat. No. 4,358,535; Berninger (U.S. Pat. No. 4,446,237), fluorescent labels (Albarella et al., EP 144914), chemical labels (Sheldon III et al., U.S. Pat. No. 4,582,789; Albarella et al., U.S. Pat. No. 4,563,417), modified bases (Miyoshi et al., EP 119448), etc. Thus, DNA probes according to the present invention include the oligonucleotide sequence alone or as part of a longer nucleic acid molecule, labeled with a detectable label, preferably a radioisotope, an enzyme, a fluorescent label, a chemical label, or a modified base.

Examples of modified or substituted nucleotides useful in constructing a labeled oligonucleotide probe of the present invention, as an alternative to a radiolabel (e.g., $^{32}$P), include the following. A base analog such as bromodeoxyuridine (BrdUrd) may be incorporated into an oligonucleotide; however, BrdUrd has the disadvantage of being highly light-sensitive. The base 5-methyl cytosine (5MC) may be used in place of cytosine in the synthesis of the probe, preferably outside the binding sequence, for example, in the form of 5MC "tail" added to the probe. An antibody specific for the modified base, such as an antibody specific for 5MC or specific for a 5MC oligomer, can be used to detect the DNA sequence. Other known modified bases may be used, provided that an antibody specific for the modified base can be prepared. After preparing a gel or blot, the target protein is detected by binding to the probe DNA of the invention, followed by a detectably labeled antibody to the substituted or modified base. Any direct or indirect antibody detection system can be used (e.g., rabbit polyclonal antiserum to 5MC plus enzyme-labeled protein A or second antibody, or a biotin-avidin sandwich method well-known in the art, etc.

Biotin can also be linked directly to DNA or an oligonucleotide fragment and its presence detected using any of a number of avidin-based detection systems well-known in the art.

Examples of the above approaches are well-known in the art of DNA detection, but can easily be adapted to use according to the present invention. For example, the method of Stavrianopoulos et al., U.S. Pat. No. 4,987,065 (Jan. 22, 1991) can be used for in vivo labeling of polynucleotide sequences, such as by incorporating a labeled base into a polynucleotide sequence, for making non-radioactively labeled probes at less cost, for use in various detection systems. Useful "label"-carrying compounds include glucosylated nucleotides, glycosylated nucleotides, 5-hydroxymethyluracil, BrdUrd and 5-methyl cytosine. Signaling moieties, which bind covalently or non-covalently to the label of the polynucleotide sequence include antibodies specific for the modified base. The method of Gratzner et al., U.S. Pat. No. 4,529,700 (Jul. 16, 1985), utilizes monoclonal antibodies (mAbs) specific for BrdUrd or specific iododeoxyuridine (IdUrd) for detection of DNA sequences by hybridization with a BrdUrd-containing probe. Sawicki et al., (1977), Science 174:70, describes antibodies specific for BrdUrd, IdUrd and 6-methyladenosine which detected these bases in denatured DNA. Thus, any form of "antigenic DNA", for example, DNA including a rare and antigenic nucleotide such as BrDUrd and IdUrd incorporated into a nucleotide sequence biosynthetically, can serve as a protein binding sequence detectable by an antibody to the rare nucleotides (Paau et al., U.S. Pat. No. 4,556,643 (Dec. 3, 1985)). BrDUrd containing DNA complexed to a protein can be detected by any of a variety of immunological techniques, such as immunoenzymatic techniques (Avrameas et al., European Patent Publication 143,059 (May 29, 1985))

The oligonucleotide probe of the present invention can be chemically modified, for example with at least one base which is covalently modified by at least one 7-iodo-N-2-acetylamino-fluorene (AAIF)(Tchen, U.S. Pat. No. 4,963, 477 (Oct. 16, 1990)). The presence of this probe is detected after binding to the protein by antibodies specific for the modified probe. Antibodies to a related structure, acetylaminofluorene, lacking the iodine (anti-AAF antibodies) made either against N-2-(guanosine-8-yl) acetylaminofluorene or against the probe bearing acetylaminofluorene residues, also recognize the modified probe.

Derivatives of the oligonucleotide of the present invention may include the oligonucleotide sequence as part of a longer nucleic acid molecule which is of natural or synthetic origin. Also included are derivatives in which the additional sequence is a mutant or variant of a naturally occurring DNA sequence. These variants or mutants ordinarily are prepared by site-directed mutagenesis (Adelman et al., *DNA* 2:183 (1983)) of DNA. Oligonucleotide or polynucleotide derivatives of oligonucleotide of the present invention typically exhibits the same qualitative activity, binding to a TRP, as the non-modified DSE oligonucleotide.

Thus, the present invention provides a method for detecting the presence of a "target" protein molecule, a TRP, in a sample. Such samples are preferably biological samples, including, but not limited to cells, cell culture supernatant, cell or tissue extracts, or particular fractions thereof, and other biological fluids such as blood, sera, urine, saliva, etc. Binding of the DNA probe to a protein in the sample may be detected by any appropriate means known in the art. Direct or indirect, or competitive binding assays may be used. Association of the label with proteinaceous material of the sample is then detected. In a preferred embodiment, the oligonucleotide sequence is modified by the addition of one or more biotin groups. Avidin, which binds to biotin with high affinity is used to detect the oligonucleotide-protein complex. The avidin can be attached to a solid support and/or labeled using any of a number of labels well-known in the art, including a radiolabel, an enzymatic label, etc.

The DNA molecules of the present invention may be included in a recombinant DNA construct which contains three operably linked sequences of interest: the protein binding sequence or "probe sequence" that acts as an "enhancer" element or part of a promoter, a "promoter sequence," and a "reporter sequence."

The "probe sequence" is a nucleic acid molecule containing an oligonucleotide sequence of the present invention or a derivative thereof capable of directly or indirectly binding to, and identifying a TRP. The TRP will then enhance the transcription of DNA operably linked to the probe sequence. An "enhancer" as used herein is a regulatory DNA sequence that (a) activates transcription from a promoter operably linked to it, with synthesis beginning at the normal RNA start site, (b) operates in both orientations, and (c) functions even when moved more than 1000 nucleotides from the promoter and from either an upstream or a downstream position. Both enhancers and promoters (see below) bind sequence-specific DNA binding proteins, such as TRPs, that mediate their effects.

The probe sequence may be a multimer of the oligonucleotide sequence comprising at least two contiguous units, preferably about 2–10 units. The multimer may also have intervening nucleotides between the individual oligonucleotide units. In fact, the oligonucleotide sequence units may also occur at multiple non-contiguous sites, preferably about 2–10 sites, in the recombinant DNA molecule, providing that the oligonucleotide units are operably linked to the promoter and reporter sequences.

A promoter is a region of a DNA (or RNA) molecule which is capable of binding RNA polymerase and promoting the transcription of an "operably linked" nucleic acid sequence. The selection of which strand is transcribed is determined by the orientation of the promoter sequence. This selection determines the direction of transcription since RNA is only polymerized enzymatically by the addition of a nucleotide 5' phosphate to a 3' hydroxyl terminus.

Two sequences of a nucleic acid molecule are said to be "operably linked" when they are linked to each other in a manner such that the presence of one sequence, e.g., the promoter, influences transcription from the linked sequence, e.g., a protein coding sequence, or a reporter sequence. Operably linked sequences may also include two segments of protein coding sequence which are transcribed onto the same RNA transcript. Thus, two sequences, such as a promoter sequence and a "reporter sequence" are operably linked if transcription commencing in the promoter sequence will produce an RNA transcript of the reporter sequence. In order to be "operably linked" it is not necessary that two sequences be immediately adjacent to one another.

The promoter sequences of the present invention may be any promoter capable of driving transcription of the reporter sequence and compatible with the host cell being studied. Thus, useful promoters may be prokaryotic, eukaryotic or viral. Examples of suitable prokaryotic promoters include promoters recognized by the T4 (Malik, S. et al., *J. Biol. Chem.* 263:1174–1181 (1984); Rosenberg, A. H. et al., *Gene* 59:191–200 (1987); Shinedling, S. et al., *J. Molec. Biol.* 195:471–480 (1987); Hu, M. et al., *Gene* 42:21–30 (1986)), T3, Sp6, and T7 (Chamberlin, M. et al., *Nature* 228:227–231 (t1970); Bailey, J. N. et al., *Proc. Natl. Acad. Sci. (U.S.A.)* 80:2814–2818 (1983); Davanloo, P. et al., *Proc. Natl. Acad. Sci. (U.S.A.)* 81.:2035–2039 (1984)) polymerases; the $P_R$ and $P_L$ promoters of bacteriophage λ (*The Bacteriophage Lambda*, Hershey, A. D., Ed., Cold Spring Harbor Press, Cold Spring Harbor, N.Y. (1973); *LAMBDA II*, Hendrix, R. W., Ed., Cold Spring Harbor Press, Cold Spring Harbor, N.Y. (1980)); the trp, recA, heat shock, and lacZ promoters of *E. coli*; the α-amylase (Ulmanen, I., et al., *J. Bacteriol.* 162:176–182 (1985)) and the σ-28-specific promoters of *B. subtilis* (Gilman, M. Z., et al., *Gene* 32:11–20 (1984)); the promoters of the bacteriophages of Bacillus (Gryczan, T. J., In: *THE MOLECULAR BIOLOGY OF THE BACILLI*, Academic Press, Inc., New York (1982)); Streptomyces promoters (Ward, J. M., et al., *Mol. Gen. Genet.* 203:468–478 (1986)); the int promoter of bacteriophage λ; the bla promoter of the β-lactamase gene of pBR322, and the CAT promoter of the chloramphenicol acetyl transferase gene of pPR325, etc. Prokaryotic promoters are reviewed by Glick, B. R., (*J. Ind. Microbiol.* 1:277–282 (1987)); Cenatiempo, Y. (*Biochimie* 68:505–516 (1986)); Watson, J. D. et al. (In: *Molecular Biology of the Gene*, Fourth Edition, Benjamin Cummins, Menlo Park, Calif. (1987)); and Gottesman, S. (*Ann. Rev. Genet.* 18:415–442 (1984)). Preferred eukaryotic promoters include yeast cyc1 promoter (Guarante et al., *Proc. Natl. Acad. Sci. USA* 78:2199–2203 (1981)), the promoter of the mouse metallothionein I gene (Hamer, D., et al., *J. Mol. Appl. Gen.* 1:273–288 (1982)); the TK promoter of Herpes virus (McKnight, S., *Cell* 31:355–365 (1982)); the SV40 early promoter (Benoist, C., et al., *Nature (London)* 290:304–310 (1981)); and the yeast gal4 gene promoter (Johnston, S. A., et al., *Proc. Natl. Acad. Sci. (USA)* 79.:6971–6975 (1982); Silver, P. A., et al., *Proc. Natl. Acad. Sci. (USA)* 81:5951–5955 (1984)). All of the above listed references are incorporated by reference herein.

In a system in which the reporter is chloramphenicol acetyl transferase (CAT), a preferred promoter is the CAT promoter of the bacterial chloramphenicol acetyl transferase gene.

The third sequence of the recombinant DNA or RNA molecules of the present invention is a "reporter sequence" which may be composed of any set of nucleotides regardless of sequence. A reporter is any gene whose product is used to assess regulation of transcription via a promoter or enhancer. The expression of the "reporter sequence" results in the formation of the "reporter molecule" which is readily detectable. Preferably, the reporter sequence will have a length of between about 5 and 3,000 bases and, more preferably, 10–100 bases. The reporter sequence will preferably be selected such that the reporter molecule will have a physical and chemical characteristics which will permit or facilitate its identification or detection by means well known in the art. In one embodiment, the presence of the reporter molecule will be detected through the use of an antibody or an antibody fragment, capable of specific binding to the reporter molecule. A reporter such as β-galactosidase or luciferase can be assayed enzymatically or immunologically.

A preferred reporter molecule is CAT, well-known in the art. See, for example, Lewin, B., *GENES IV*, Oxford University Press, 1990, chap. 23 ). Because this is a bacterial gene, it is absent from eukaryotic cells and the enzyme product can be directly assayed in a cell extract. The level of enzyme activity corresponds to the amount of enzyme that was made, which in turn reveals the level of expression. CAT mRNA may also be measured directly. Typically, a plasmid containing the recombinant DNA molecule of the present invention, including the CAT gene, is introduced into eukaryotic cells (which may be designated "reporter cells"), which are then grown for several days. The reporter cells are treated with the test material suspected of containing a material capable of inducing or activating a TRP, for example, an extract of other cytokine-treated cells. The CAT-producing reporter cells are extracted, $^{14}$C-chloramphenicol is added, the reaction incubated about 60 minutes, and the extract is run on thin layer chromatography to separate acetylated and nonacetylated forms and assayed by autoradiography. Total acetylated chloramphenicol corresponds to the units of CAT enzyme activity.

When transcription of CAT is activated by the TRP being assayed, CAT synthesis is increased relative to a control lacking the TRP. Thus, the amount of CAT enzyme produced is an indirect measure of transcription induced by the TRP binding to the oligonucleotide sequence of the present invention which is operably linked to the CAT gene.

Cytokines or growth factors may induce any of a number of yet undiscovered TRPs which bind to the DNA sequence of the present invention. Thus, the present invention is further directed to a protein, other than p91, inducible in a cell by a cytokine, growth factor or hormone, which protein binds to the DNA sequence TTTCCGGGAAA (SEQ ID NO:2) or to the double stranded sequence

| | |
|---|---|
| 5'-gatcTAGGGATTTCCGGGAAATGAAGCT-3' | SEQ ID NO:3 |
| 3'ATCCCTAAAGGCCCTTTACTTCGActag-5' | SEQ ID NO:4 |

Such a protein may be induced by any cytokine or growth factor, such as those described above. Preferably, the protein is induced by IL2, IL3 or erythropoietin. This protein is preferably a TRP, either stimulatory or inhibitory.

PROTEIN ISOLATION AND PURIFICATION

The invention provides a naturally occurring TRP protein other than p91 substantially free of other proteins or glycoproteins with which it is natively associated. "Substantially free" indicates that the protein has been purified away from at least 90% (on a weight basis), and from even at least 99% if desired, of other proteins and glycoproteins with which it is natively associated, and is therefore substantially free of them.

Such purification can be achieved by subjecting the cells, tissue or fluids containing the TRP to standard protein purification techniques. In particular, the present invention provides novel methods for the isolation and purification of TRPs. These methods are based on affinity chromatography, which relies on the interaction of the protein to be purified with an immobilized ligand. Here, the ligand for a TRP is an oligonucleotide or derivative of the present invention. This ligand may be able to react with a number of TRPs and thus serves as a means for recovering a particular class of proteins.

In a preferred embodiment, the oligonucleotide of the present invention is immobilized on a solid support or carrier. By "solid phase carrier or support" is intended any support capable of binding the oligonucleotide or DNA molecule of the present invention. Well-known supports, or carriers, include glass, polystyrene, polypropylene, polyethylene, dextran, nylon, amyloses, natural and modified celluloses, polyacrylamides, agaroses, and magnetite. Methods for coupling nucleic acids to the solid phase, the solid phase substances useful in these methods, and means for elution, are well known to those of skill in the art. The protein bound to the DNA directly or indirectly may be eluted from the solid phase using any of a number of methods well-known in the art.

In addition to the specific methods described above, purification steps prior to affinity purification may include one or more standard method, such as ammonium sulfate precipitation, size exclusion chromatography (gel filtration), ion exchange chromatography, differential precipitation and the like, all well-known in the art. Also useful is the method known as hydrophobic interaction chromatography (HIC) which is based on the interaction between the solute and the gel that is hydrophobic. Hydrophobic interactions are strongest at high ionic strength, therefore, this form of separation is conveniently performed following salt precipitations or ion exchange procedures. Elution from HIC supports can be effected by alterations in solvent, pH, ionic strength, or by the addition of chaotropic agents or organic modifiers, such as ethylene glycol. General principles of HIC are described in U.S. Pat. Nos. 3,917,527 and 4,000,098. Purification of specific proteins using HIC is disclosed in the following U.S. Patents: U.S. Pat. No. 4,332,717; U.S. Pat. No. 4,771,128; U.S. Pat. No. 4,743,680; U.S. Pat. No. 4,894,439; U.S. Pat. No. 4,908,434; and U.S. Pat. No. 4,920,196.

The DSE oligonucleotide or a functional derivative thereof, according to the present invention, can be used to assay for TRPs at any stage of a purification process as described above.

Having now generally described the invention, the same will be more readily understood through reference to the following examples which are provided by way of illustration, and are not intended to be limiting of the present invention, unless specified.

EXAMPLE I

Stimulated 3T3 Cells or Fibroblasts Produce DNA-Binding Proteins

A. MATERIALS AND METHODS

3T3 cells were treated with PDGF for 15 min, and nuclear and cytoplasmic extracts. Protein extracts from nuclei or cytoplasm of cells treated with various cytokines were prepared and tested for binding to a SIF recognition DNA sequence by electrophoretic gel band shift in an assay previously described (D. E. Levy et al., Genes Dev. 3, 1362 (1989); D. S. Kessler et al., Genes Dev. 4, 1753 (1990)). The DNA probe used $^{32}$P-labeled, double-stranded oligonucleotide with the sequence 5'-GATCAGCTTCATTTCCCGTAAATCCCTA-3' (T. E. Hayes et al., Proc. Natl. Acad. Sci. USA 84, 1272 (1987); B. J. Wagner et al., EMBO J. 9, 4477 (1990)). Also tested was a modified oligonucleotide sequence (DSE in Table I, above), which binds the same proteins with higher apparent affinity.

Cells were incubated in medium containing 0.5% serum for 24-48 h prior to treatment with cytokines.

B. RESULTS

1. PDGF-Treated 3T3 Cells

Figure 1A:
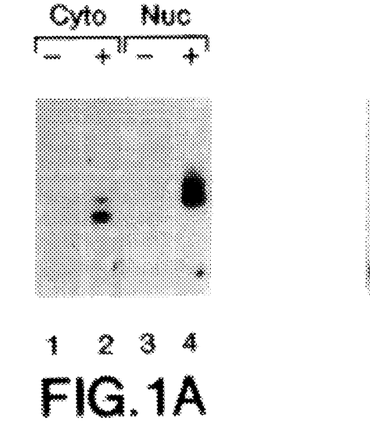

Little or no specific DNA binding activity was present in extracts from untreated cells while abundant activity was readily detected in extracts from PDGF-stimulated cells (FIG. 1A). DNA binding activity was detected in both cytoplasmic (lane 2) and nuclear fractions (lane 4), suggesting cytoplasmic activation followed by nuclear translocation similar to ISGF3 (Kessler et al., supra; Dale et al., supra). Similar cytoplasmic activation of SIF was reported (H. B. Sadowski et al., Nature 362, 79 (1993)); furthermore, latent SIF DNA binding activity could be stimulated in vitro in cytoplasmic extracts supplemented with membranes, reinforcing the conclusion that factor activation occurs in the cytoplasm.

2. EGF-Treated Human Fibroblasts

Figure 1B:
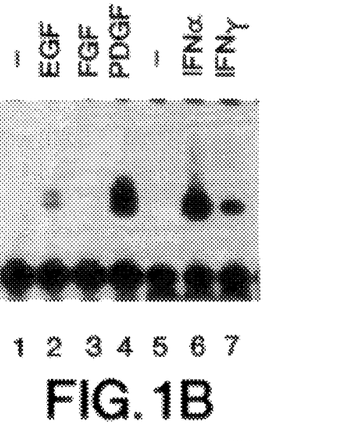
Figure 1C:
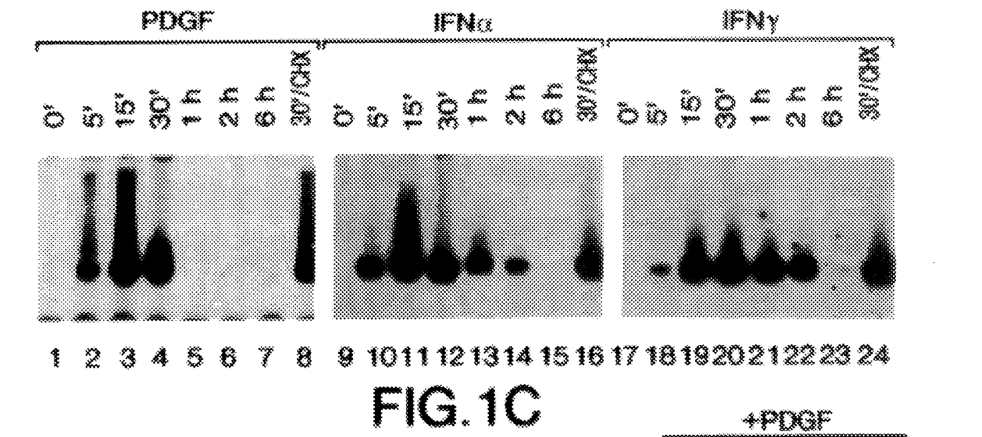

SIF DNA-binding activity was also detected in extracts from human fibroblasts treated with EGF (FIG. 1B, lane 2), but not in untreated cells (lanes 1 and 5) or in cells treated with FGF (lane 3). Surprisingly, SIF band shift activity was also detected in extracts of cells treated with either IFNα or IFNγ (lanes 6 and 7). Activation by PDGF, IFNα, and IFNγ was rapid, occurring within 5 min, transient, and resistant to inhibition of protein synthesis by cycloheximide (FIG. 1C). Duration of the responses differed: SIF was undetectable after 1 h of PDGF treatment (lane 5) while it was still detectable for up to 6 h in response to IFNγ (lane 23). Interestingly, SIF activation occurred in cells treated with PDGF at 4° C. while IFN activation required a 37° C. incubation (O. Silvennoinen, D. E. Levy, unpublished data.).

Figure 1D:
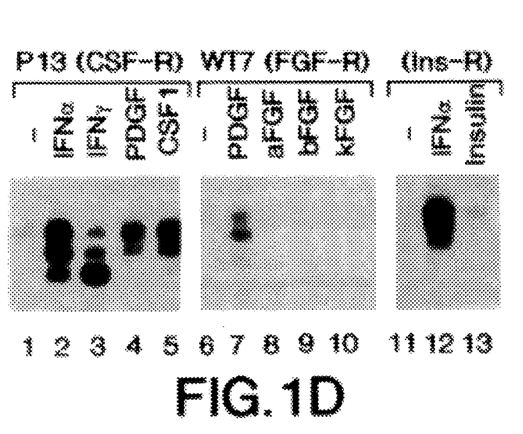

The specificity of SIF activation was tested in cell lines overexpressing growth factor receptors (FIG. 1D). Mouse fibroblasts expressing the mouse colony stimulating factor 1 (CSF1) receptor (M. Mohammadi et al., Nature 358, 681 (1992)) responded to CSF1 treatment by stimulating SIF DNA-binding activity (lane 5). However, acidic, basic, and k-FGF failed to activate SIF in FGF-responsive, Swiss 3T3 cells or in WT7 cells (M. Mohammadi et al., Nature 358, 681 (1992)) overexpressing the FGF receptor 1 (flg) gene (lanes 8-10). Likewise, insulin treatment (lane 13) did not lead to SIF activation in cells overexpressing the human insulin receptor (C. K. Chou et al., J. Biol. Chem. 262, 1842 (1987)). These cell lines could be stimulated to activate SIF binding activity in response to PDGF or IFN (lanes 7 and 12). Despite absence of SIF stimulation by FGFs and insulin, all these growth factors caused receptor autophosphorylation and an increase in tyrosine phosphorylation of cellular proteins.

Figure 1E:
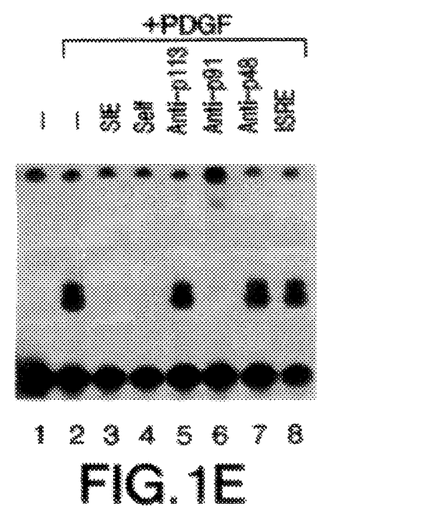

Comparison of the SIF DNA sequence with IFNγ response elements (R. N. Pearse et al., Proc. Natl. Acad. Sci. USA 90, 4314 (1993)) suggested that it might serve as a binding site for the 91 kDa subunit of ISGF3a (p91). To test this possibility, band shift reactions were treated with antibodies to the different components of ISGF3 (FIG. 1E). The PDGF-stimulated band shift was unaffected by antibodies to the p48 and p113 components of ISGF3; in contrast, this DNA-binding activity was abrogated by antibodies to p91, concomitant with the appearance of a more slowly migrating super-shifted complex (lanes 5–7). Specificity of DNA-binding was demonstrated by competition with SIF-binding sequences (lanes 3 and 4) but absence of competition by an irrelevant sequence (the ISRE, lane 8). Similar involvement of p91 could be demonstrated for the binding activity stimulated by both IFNα and IFNγ.

EXAMPLE II

Tyrosine Phosphorylation in p91 Activation

Figures 2A, 2C:
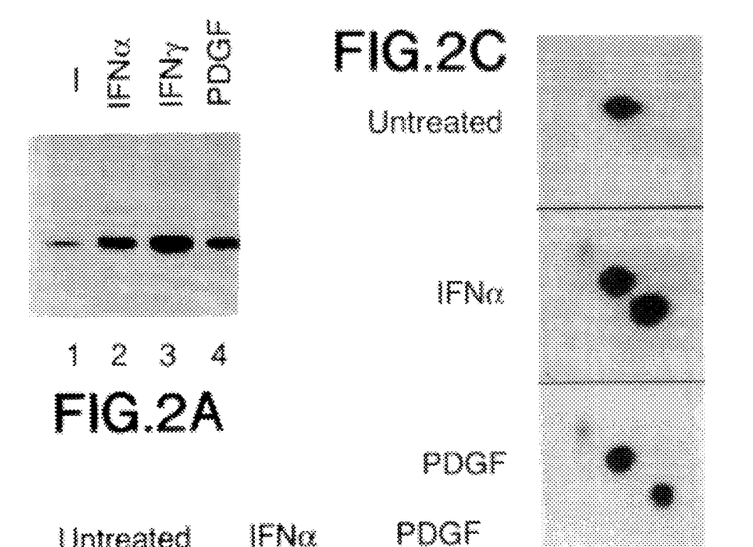
FIGS. 2A–2D show tyrosine phosphorylation of p91 by PDGF and interferons.
Figure 2B:
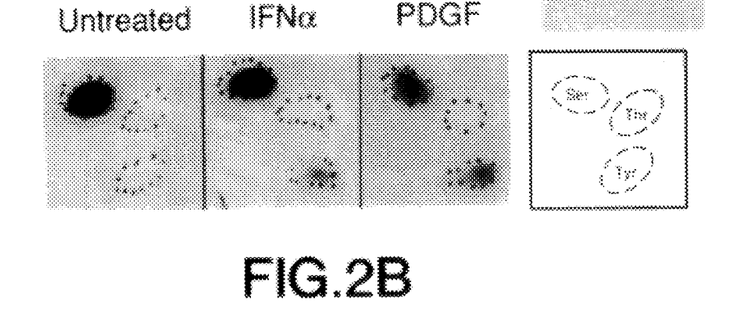

To test the involvement of tyrosine phosphorylation in p91 activation, cells were labeled with $^{32}$P-orthophosphate and treated with IFNs or growth factors. Human FS2 fibroblasts were labeled with $^{32}$P-orthophosphate (0.8 mCi/ml) for 2 h and either left unstimulated or stimulated with IFNα, IFNγ, or PDGF, as indicated. Lysates were subjected to immunoprecipitation using anti-p91c sera (C. Schindler et al., Science 257, 809 (1992)) and analyzed by SDS-PAGE, phosphoamino acid analysis, and phosphopeptide analysis, as previously described (W. Li et al., Mol. Cell. Biol. 12, 5824 (1992)). Immunoprecipitation of labeled extracts with anti-p91 showed a stimulation of phosphorylation of this protein in response IFNα, IFNγ, and PDGF (FIG. 2A). p91 precipitated from IFNα-treated cells (lane 2) co-precipitated with the 113 kDa subunit of ISGF3 (Schindler et al., supra). However, this protein was not detected in samples from IFNγ-treated or PDGF-treated cells (lanes 3 and 4). This reflects the exclusive activation of p113 in response to IFNα, while p91 phosphorylation occurs in response to all three ligands. Phosphoamino acid analysis revealed the presence of phosphotyrosine in p91 exclusively from treated samples, while untreated samples contained only phosphorylated serine residues (FIG. 2B). Peptide map analysis of tryptic digestion products revealed phosphorylation of the same, single new tryptic phosphopeptide in response to all three agents (FIG. 2C).

Figure 2D:
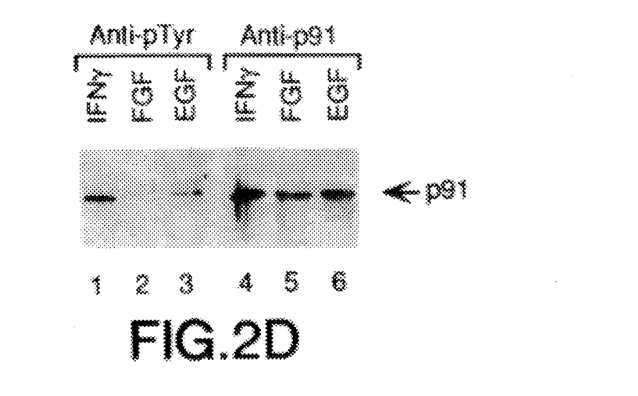

Further demonstration of tyrosine phosphorylation of p91 in response to growth factors involved immunoblotting with anti-phosphotyrosine antibodies (FIG. 2D). Proteins from cells treated with various factors were immunoprecipitated with anti-p91, fractionated by SDS-PAGE, and transferred to nitrocellulose. Cells were lysed in 50 mM Tris, pH 7.5, 150 mM NaCl, 1% Triton X-100, 500 µM sodium orthovanadate, 1 mM EDTA, 1 mM PMSF, 3 µg/ml aprotinin, 0.5 µg/ml leupeptin and immunoprecipitated with anti-p91c sera. Immune complexes were separated on SDS-PAGE, transferred to nitrocellulose, analyzed using anti-phosphotyrosine monoclonal antibodies (Upstate Biotechnology, ICN, and Oncogene Science) or anti-p91c and HRP-labeled second antibody, and detected by enhanced chemiluminescence (Amersham).

A 91-kDa band could be detected with anti-pTyr antibodies in extracts from IFN- or EGF-treated cells (lanes 1 and 3), but not from cells treated with FGF (lane 2). Thus, the 91 kDa subunit of ISGF3, or a protein closely related to it, is tyrosine phosphorylated in response to a number, but not all, growth factors, leading to its nuclear accumulation and its ability to bind specifically to DNA regulatory elements. The absence of SIF binding activity in FGF-treated cells is therefore due to the inability of this growth factor to stimulate tyrosine phosphorylation of p91.

EXAMPLE III

Involvement of EGF Receptor in p91 Activation

Figures 3A, 3B:
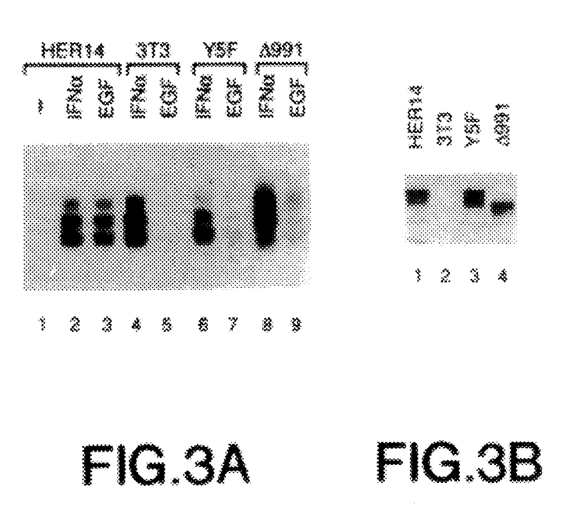
FIGS. 3A–3D shows that activation of p91 requires receptor autophosphorylation but is independent of Ras.

The mitogenic action of EGFR and other receptor tyrosine kinases appears to signal through Ras and may require intervention by intermediary proteins specifically recognizing the autophosphorylated cytoplasmic tail of the receptor. To test the involvement of the EGFR in tyrosine phosphorylation of p91, cells expressing different mutant human EGFRs (N. Li et al., unpublished data) were activated with EGF or with IFNα (FIG. 3A). Only cells expressing wild-type receptor (lane 3) showed full stimulation of p91 in response to EGF. Truncation of the EGFR cytoplasmic tail, leaving only the kinase catalytic domain and removing the major autophosphorylated tyrosines, greatly diminished the ability of EGF to stimulate p91 (lane 9). Likewise, mutation of the five autophosphorylation sites to the phenylalanine residue also prevented the normal induction of p91 DNA-binding activity in response to EGF (lane 7), in spite of similar levels of receptor expression (FIG. 3B).

In contrast to their responses EGF stimulation, all cells responded normally to IFNα (lanes 2, 4, 6, and 8). This result suggests that tyrosine autophosphorylation of the receptor is required for p91 activation. Possibly, p91, an SH2-domain containing protein (C. Schindler et al., *Proc. Natl. Acad. Sci. USA* 89:7836 (1992); X.-Y. Fu, *Cell* 70, 323 (1992)), is recruited directly to a tyrosine kinase activated by EGF stimulation by recognition of phosphorylated tyrosine residues. Indeed, Sadowski et al. (supra) found that an SH2 domain-containing protein and antibodies to phosphotyrosine prevented SIF activation in vitro (Sadowski et al., supra).

Mutations eliminating tyrosine autophosphorylation sites on EGFR have little effect on the mitogenic properties of EGF (S. J. Decker, *J. Biol. Chem.* 268, 9176 (1993)); hence, p91 activation, which requires receptor autophosphorylation, may occur independently of mitogenesis.

Figure 3C:
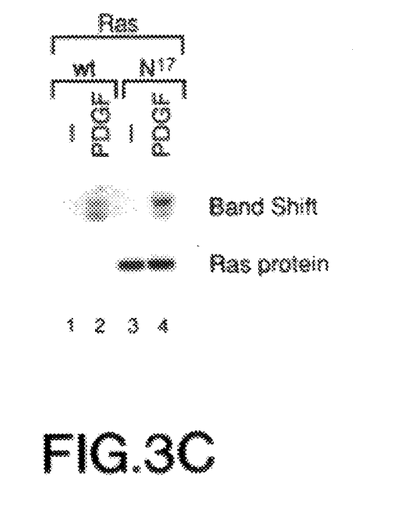
Figure 3D:
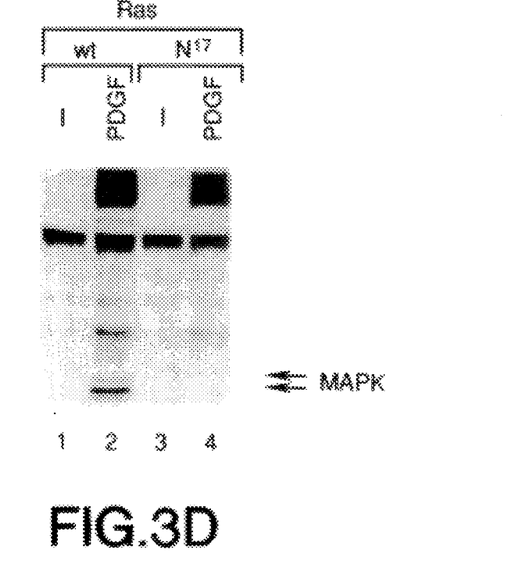

To further assess the connection between p91 activation and mitogenesis, we investigated the involvement of Ras in p91 action in cells expressing dominant-negative mutations of H-Ras. Mutation of serine to asparagine at position 17 of H-Ras (N$^{17}$-Ras) prevents guanine nucleotide exchange, inhibiting Ras activation in a dominant fashion and suppressing mitogenic responses to growth factors (D. W. Stacey et al., *Oncogene* 6, 2297 (1991); D. W. Stacey et al., *Mol. Cell. Biol.* 11, 4053 (1991)). In both parental type cells and cells expressing N$^{17}$-Ras (E. Y. Skolnik et al., *Science* 260, 1953 (1993)), PDGF stimulated p91 DNA-binding activity (FIG. 3C, top), despite abundant levels of mutant Ras proteins (bottom). However, the N$^{17}$-Ras mutation prevented the Ras-mediated activation of MAP kinase by PDGF (FIG. 3D), an essential step in PDGF-induced mitogenesis.

GENERAL DISCUSSION OF EXAMPLES I–III

Figure 4:
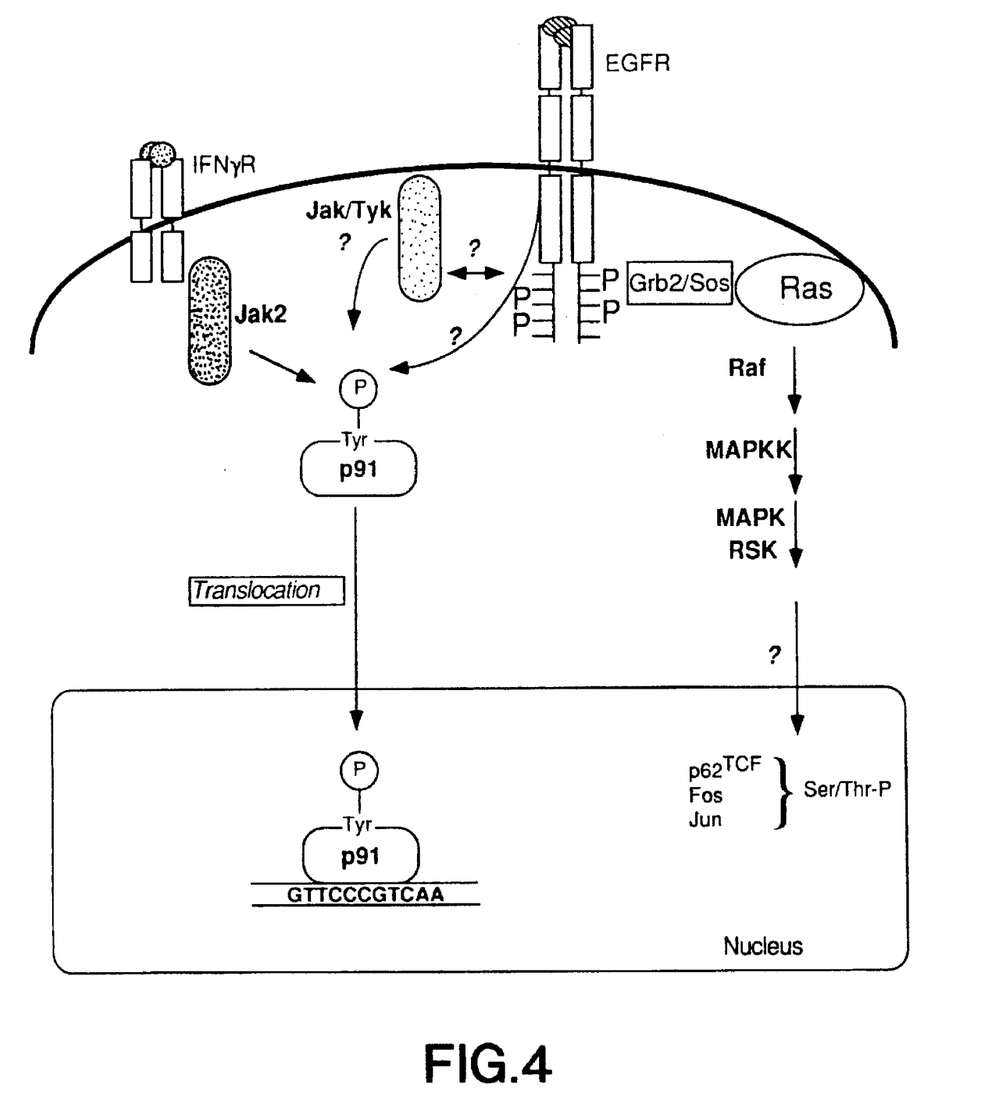

The present findings point to a distinct mechanism for growth factor signaling, directly linking receptor tyrosine kinase activation to modulation of nuclear events. This is schematically illustrated in FIG. 4.

EGF, PDGF, and CSF1 stimulated the tyrosine phosphorylation of a latent, cytoplasmic transcription factor, causing it to translocate to the nucleus and acquire the ability to bind DNA; this effect is similar to that observed by stimulation of IFN receptors which are not tyrosine kinases. This pathway is independent of Ras and the action of MAP kinase, which are thought to lead to activation of the fos promoter through ser/thr phosphorylations (S. A. Moodie et al., supra; Lange-Carter et al., supra).

Recent studies showed that the tyrosine kinase Tyk2 is necessary for IFNα signaling (L. Velazquez et al., *Cell* 70, 313 (1992)), and the related enzyme Jak2 appears to mediate IFNγ action. Cytoplasmic tyrosine kinases may also be necessary for growth factor stimulation of p91.

The biologic significance of activation of a common transcription regulatory factor shared by mitogenic growth factors and by anti-proliferative, differentiation-stimulating cytokines is still unclear. Receptor tyrosine kinases can stimulate cells to proliferate or to differentiate and withdraw from the cell cycle depending upon cellular context and specific culture conditions (J. den Hertog et al., *Cell Growth Diff.* 2, 155 (1991)). Indeed, CSF1 stimulates mitogenesis when of fibroblasts transfected with the CSF1 receptor (Roussel et al., supra) but fulfills distinct signaling functions during macrophage differentiation and osteoclast activation. Likewise, EGF, FGF, and NGF can stimulate either cell division or neurite outgrowth in pheochromocytoma cells (J. Schlessinger et al., *Neuron* 9, 383 (1993)). Differential activation of distinct sets of genes following activation of ligand-specific sets of latent transcription factors may therefore modulate the outcome of a simultaneous, Ras-mediated common signal.

One might expect a lack of specificity to result from multiple signaling pathways impinging on a single transcription factor, ISGF3 p91. A potential solution is suggested by studies of IFN induction, wherein IFNα and IFNγ, both of which stimulate tyrosine phosphorylation of p91, nevertheless lead to the activation of distinct sets of genes (K. Shuai et al., supra; R. N. Pearse et al., supra; Y. Kanno et al., supra). However, only IFNα leads to the additional tyrosine phosphorylation of the 113 kDa transcription factor subunit (C. Schindler et al., *Science* 257, 809 1992)), while IFNγ and PDGF activate only p91 (see FIG. 2A). Assembly of activated p91 and p113 into the ISGF3a complex following IFNα treatment allows association with the 48 kDa ISGF3g subunit (D. E. Levy et al., *Genes Dev.* 3, 1362 (1989); D. S. Kessler et al., *Genes Dev.* 4, 1753 (1990)), a protein with a distinct DNA-binding specificity that directs the complex to a regulatory element unique to IFNα-stimulated genes (S. A. Veals et al., *Mol. Cell. Biol.* 12, 3315 (1992)).

The complete ISGF3 complex displays a DNA-binding specificity distinct from that of any of the individual subunit proteins on their own (S. A. Veals et al., *Mol. Cell. Biol.* 13, 196 (1993)). Similar specificity-determining subunits analogous to p48 and p113 may be involved in each signaling pathway from a distinct receptor, combining with the common p91 sub-unit and directing the complex to appropriate target genes. The absence of p91 involvement in insulin and FGF signaling suggests yet further complexity. Possibly, a unique specificity of insulin or FGF receptors for proteins with distinct SH2 domains could direct them to activate distinct cytoplasmic transcription factors. Combinatorial assembly of these different subunits would result in a high degree of potential signaling specificities.

EXAMPLE IV

Comparison of Protein Binding to the DSE Oligonucleotide Sequence and the SIE Oligonucleotide Sequence Nuclear extracts (5 µg) from Swiss 3T3 cells were treated for 15 min with 2500 u/ml murine IFNα and the extracts mixed with $^{32}$P-labeled DSE. The binding of proteins in the extract to the oligonucleotide were measured in a 5 µl gel band shift reaction. Each reaction contained 1.8 µg of non-specific competitor DNA plus an excess of competitor oligonucleotide. Gel band shift reactions were resolved on 5% acrylamide gels.

Figure 5:
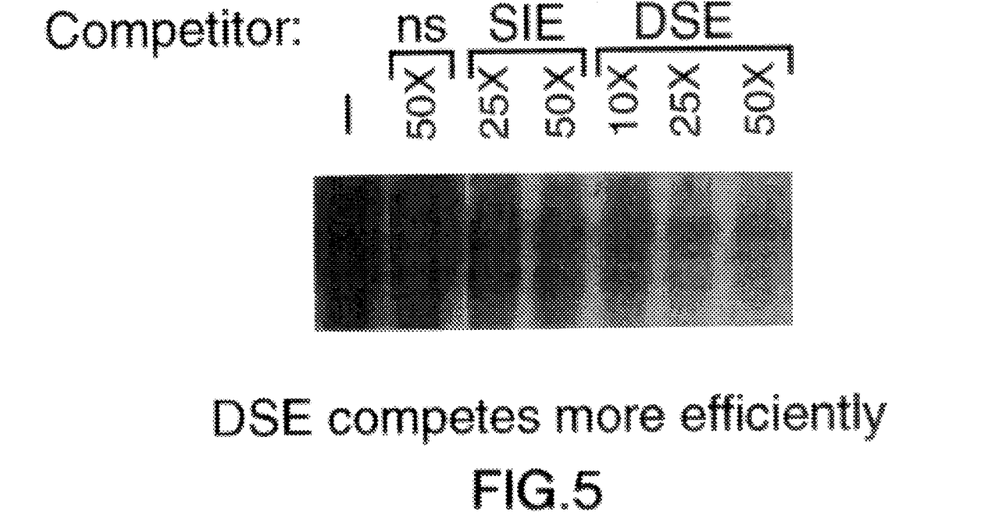

The results are shown in FIG. 5. Tenfold molar excess of DSE competed equally to 50-fold excess of SIE. Thus, proteins bind the DSE sequence with higher affinity than to the SIE oligonucleotide sequence. Thus, the DSE oligonucleotide, or a larger oligonucleotide containing the DSE sequence is useful as a probe for detecting a TRP-type of DNA binding protein, for isolating such a protein, and for measuring the activity of such a protein.

EXAMPLE V

Induction of DSE-Binding Proteins by Interleukin-2, Interleukin-3 and Erythropoietin Cells responsive to particular cytokines or growth factors were used to test the induction of proteins which bind to the DSE-containing oligonucleotide. BaF3/ER cells (D'Andrea et al. (1991) *Molec. Cell. Biol.* 11:1980–1987), responsive to erythropoietin and IL3, were grown in the absence of either erythropoietin or IL-3. LyD9, responsive to IL-3, cells were grown for 4 hr in the absence of IL-3. CTLL cells (ATCC TIB214), responsive to IL-2, were grown for 4 hr in the absence of IL2. The cells were then treated with their appropriate cytokine/growth factor for 15 minutes. Nuclear extracts (5 µg) prepared from each of the treated cell populations, as well as unstimulated control cells, were analyzed by gel band shift assays, as described above, using a $^{32}$P-DSE probe.

Figure 6:
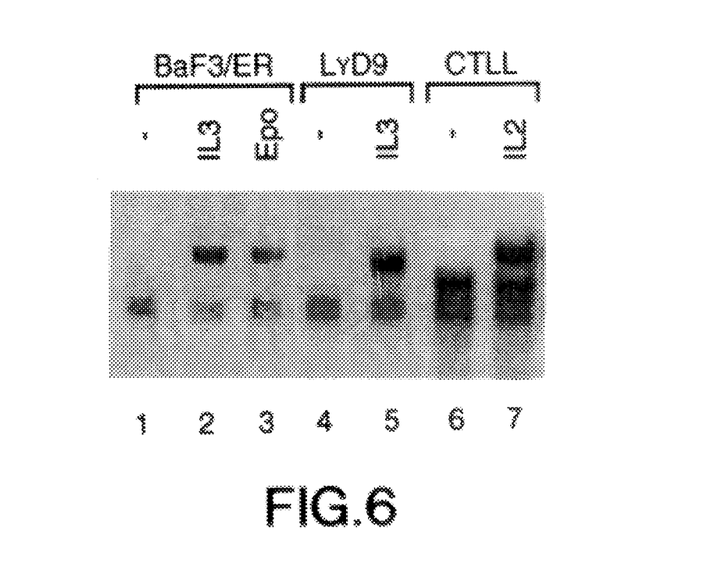

The results, shown in FIG. 6, indicate that DSE-binding proteins are induced in these cells by the cytokine/growth factor to which they are responsive: erythropoietin, IL-2 or IL-3. It is note-worthy that the IL-2 and IL-3 resulted in a DNA-protein complex of a different molecular weight than that induced by IFNα. Furthermore, the present inventors found that an antibody specific for p91 does not bind to the TRPs induced by IL-2, IL-3 or erythropoietin. These results indicate that novel TRPs which bind to the DSE oligonucleotide sequence are induced by IL-2, IL-3 and erythropoietin.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

---

What is claimed is:

1. A method for detecting the presence in a sample of a transcriptional regulatory protein which binds to an oligonucleotide or to a molecule to which said oligonucleotide is bound, which oligonucleotide
   i) has between 11 and about 150 nucleotides,
   ii) binds to transcriptional regulatory protein p91 or to a protein to which p91 is bound, and
   iii) comprises the nucleotide sequence TTTCCNGGAAA (SEQ ID NO:1), which method comprises:
      (a) contacting said sample with said oligonucleotide under conditions wherein said protein binds to said oligonucleotide to form a complex; and
      (b) detecting the presence of said protein-oligonucleotide complex,
   wherein the presence of said complex indicates the presence of said protein in said sample.

2. A method for determining whether a protein in a sample is a DNA-binding protein with transcriptional regulatory protein activity, comprising
   (a) contacting the sample with an oligonucleotide which
      i) has between 11 and about 150 nucleotides,
      ii) binds to transcriptional regulatory protein p91 or to a protein to which p91 is bound, and
      iii) comprises the nucleotide sequence TTTCCNGGAAA (SEQ ID NO:1); and
   (b) detecting the binding of protein in said sample to said oligonucleotide.

3. A method for detecting the presence or measuring the activity of a compound in a sample, which compound is capable of inducing in a cell a transcriptional regulatory protein which binds to DNA and stimulates transcription, which method comprises:
   (a) contacting the sample with a host cell transformed or transfected with a recombinant DNA molecule comprising an oligonucleotide having the following properties:
      i) has between 11 and about 150 nucleotides,
      ii) binds to transcriptional regulatory protein p91 or to a protein to which p91 is bound,
      iii) comprises the nucleotide sequence TTTCCNGAAA (SEQ ID NO:1), and
      iv) is operably linked to a promoter, which promoter is operably linked to an expressible reporter nucleotide sequence under conditions in which said expressible reporter sequence is expressed;
   (b) measuring the expression of said reporter sequence;
   (c) comparing said expression in step (b) with the expression of expressible reporter sequence not linked to said oligonucleotide
   wherein an increase in the expression of said expressible reporter sequence indicates the presence of, or the activity of, said compound in said sample.

* * * * *

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:1:

TTTCCNGGAA A                                                                     1 1

( 2 ) INFORMATION FOR SEQ ID NO:2:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:2:

TTTCCGGGAA A                                                                                                11

( 2 ) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:3:

GATCTAGGGA TTTCCGGGAA ATGAAGCT                                                                              28

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:4:

ATCCCTAAAG GCCCTTTACT TCGACTAG                                                                              28

( 2 ) INFORMATION FOR SEQ ID NO:5:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:5:

GTTCCCGTCA A                                                                                                11

( 2 ) INFORMATION FOR SEQ ID NO:6:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:6:

TTTACGGGAA                                                                                                  10

( 2 ) INFORMATION FOR SEQ ID NO:7:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:7:

TTTAGAGTAA T                                                                                                11

( 2 ) INFORMATION FOR SEQ ID NO:8:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:8:

TTTATAGTAA G                                                                                                11

( 2 ) INFORMATION FOR SEQ ID NO:9:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:9:

TTTCTGGGAA A                                                                                                             11

( 2 ) INFORMATION FOR SEQ ID NO:10:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:10:

ATTTGGAGAA A                                                                                                             11

( 2 ) INFORMATION FOR SEQ ID NO:11:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:11:

AGTGATTTCT CGGAAAGAGA G                                                                   21

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:12:

CATCATTTCG GGGAAATCAG G                                                                   21

( 2 ) INFORMATION FOR SEQ ID NO:13:

( i ) SEQUENCE CHARACTERISTICS:
        ( A ) LENGTH: 11 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:13:

AAAGGCCCTT T                                                                                         11

( 2 ) INFORMATION FOR SEQ ID NO:14:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear     ( x i ) SEQUENCE DESCRIPTION: SEQ ID NO:14:

GATCAGCTTC ATTTCCCGTA AATCCCTA                                           28